United States Patent [19]
Cuscurida et al.

[11] Patent Number: 5,256,828
[45] Date of Patent: Oct. 26, 1993

[54] HETEROGENEOUS CATALYST FOR ALKOXYLATION OF ALCOHOLS

[75] Inventors: Michael Cuscurida; John F. Knifton, both of Austin; Pei-Shing E. Dai, Port Arthur, all of Tex.

[73] Assignee: Texaco Chemical Company, White Plains, N.Y.

[21] Appl. No.: 22,843

[22] Filed: Feb. 25, 1993

Related U.S. Application Data

[63] Continuation-in-part of Ser. No. 896,841, Jun. 12, 1992, abandoned.

[51] Int. Cl.⁵ ............................................. C07C 41/03
[52] U.S. Cl. ...................................... 568/620; 502/79
[58] Field of Search ........................................ 568/620

[56] References Cited

U.S. PATENT DOCUMENTS 3,539,648  11/1970  Orkin .................................. 568/620

Primary Examiner—Howard T. Mars
Attorney, Agent, or Firm—James L. Bailey; Kenneth R. Priem; Cynthia L. Kendrick

[57] ABSTRACT

Disclosed is a process for producing narrow range glycols which comprises reacting a glycol with ethylene oxide in the presence of a heterogeneous catalyst consisting essentially of an alkali metal, alkaline earth metal or alkali metal halide impregnated into an inorganic solid oxide selected from the groups consisting of small pore faujasite zeolites, pentasil zeolites, small pore ferrierite zeolites, two-dimensional mordenite zeolites, β-type zeolite, basic zeolites and Group IV oxides or mixtures thereof.

13 Claims, No Drawings

HETEROGENEOUS CATALYST FOR ALKOXYLATION OF ALCOHOLS

This is a continuation-in-part of application Ser. No. 07/896,841, filed Jun. 12, 1992, now abandoned.

FIELD OF THE INVENTION

This invention relates to an improved process and a catalyst for the preparation of narrow range glycols. More particularly, this invention relates to a method for the alkoxylation of diethylene glycol with ethylene oxide by passing the reactant over a heterogeneous catalyst comprising a compound from the group consisting of alkali metals, alkaline earth metals and alkali metal halides impregnated or exchanged into an inorganic solid oxide selected from the group consisting of zeolites generally having pore dimensions less than about 10 Å and oxides of Group III and/or IV of the Periodic Table and mixtures thereof.

This process is advantageous in that it is much more selective toward the formation of triethylene glycol(-TEG) than any method currently available, produces fewer "heavy" materials, could be used in a continuous reactor, and allows for catalyst removal by simple filtration.

BACKGROUND OF THE INVENTION

A variety of different types of zeolites is known in the art, including natural and synthetic zeolites. Research has opened up a spectrum of new opportunities in the field of molecular shape selective catalysis, where the intracrystalline space accessible to molecules has dimensions near those of the molecules themselves. This field is discussed in an article titled "Molecular Shape Selective Catalysis", P. B. Weisz, New Horizons in Catalysis, Part A, 1980. For example, it is possible to catalyze the dehydration of n-butanol over a Linde 5 Å zeolite without reacting isobutanol which may be present. Such research has led to the concept of molecular engineering.

Early work was very limited by the choice of zeolites. This limitation lead to the discovery of methods for zeolite synthesis, using large organic cations as templates in place of the traditional all-inorganic ionic species. This research opened the way to the synthesis of many new zeolites. Now a number of industrial processes, including selectoforming, M-forming, dewaxing, xylene isomerization, ethyl benzene production, toluene disproportionation and methanol-to-gasoline are based on shape selective zeolites. Since the early demonstrations of product selectivity, many more cases have been observed and many reviewed and reported by Csicsery and Derouane. See S. M. Csicsery, "Zeolite Chemistry and Catalysis", ACS Monograph 171, J. A. Rabo, Ed., American Chemical Society, Washington, D.C.(1976), and E. G. Derouane, "Diffusional Limitations and Shape Selective Catalysis in Zeolites", from Intercalation Chemistry, M. S. Whittinham, A. J. Jacobson, Eds., Academic Press, New York.

There is a review of molecular sieve zeolites used in catalysis titled "Molecular Sieve Catalysis", J. W. Ward, Applied Ind. Catal., Vol. 3, 1984. Though zeolites have been known for a long time, the major stimulus in molecular sieve science came with the first synthesis of A zeolite by Milton, described in U.S. Pat. No. 2,882,243 (1959).

The natural crystalline aluminosilicate zeolites can be represented by the empirical formula:

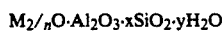

The synthetic X and Y type zeolites have framework structures similar to that of the natural mineral faujasite although they are distinct species. The unit cells are cubic with a cell dimension of nearly 25 Å. Each unit cell contains 192 $SiO_4$ and $AlO_4$ tetrahedra that are linked through shared oxygen atoms. Ibid., p.274.

In the Y zeolites the three-dimensional framework comprising a tetrahedral arrangement of connected truncated octahedral provides giant supercages approximately 13 Å in diameter with eight supercages per unit cell. The supercages are interconnected by twelve-membered rings of about 8 Å in diameter. Many different chemical species can be absorbed by this large-pore system. Ibid., p. 275.

Various zeolites have characteristic structures which favor certain types of reactions. For instance, mordenite is one of the most silica-rich zeolite minerals, having a $SiO_2/Al_2O_3$ ratio of about 10. The structure consists of chains of tetrahedra cross-linked by the sharing of oxygen atoms. Mordenite has high thermal stability, probably due to the presence of the large number of five-membered rings that are energetically favored. The dehydrated structure has a two-dimensional channel system accessible to small molecules, but not to typical hydrocarbon molecules. Ibid., pp. 275-6.

Erionite is probably the smallest pore zeolite used commercially.

A number of zeolites and molecular sieves have been synthesized that have $SiO_2$-$Al_2O_3$ ratios greater than 10 or are essentially pure silicas. Examples of those which have found commercial utility because of their shape selective properties are ZSM-5 and ZSM-11. Some of these zeolites are aluminum-free silicalites which have no ion-exchange properties and should properly be regarded as molecular sieves.

Zeolite molecular sieves can be modified by treatment by cation exchange, thermal or hydrothermal treatment and chemical modification. Most catalytic preparations involve an ammonium ion exchange, typically by refluxing the zeolite with at least a five-fold excess of aqueous ammonium salt.

Divalent cation exchange with elements such as calcium and magnesium is considered rather difficult according to Ward.

Rare earth ion exchange zeolites have played an important role in zeolite catalysis, particularly in fluid cracking catalysts and require multiple batch exchanges at elevated temperatures with excess solutions. Ibid., pp. 288-289.

Zeolites having higher silica/alumina ratios are more stable and, therefore, more suitable for treatment. Careful acid treatment can result in up to 75% of the alkali metal ions being replaced before structural collapse occurs. Ibid., p. 290.

The thermal or hydrothermal treatment of zeolites is also known. Thermal treatment of synthesized X and Y zeolites has no structural effects on the zeolite until the decomposition temperature of about 800° C. is reached. It is possible to exchange and reexchange ions. For instance, it is possible to exchange with ammonium ions, calcine and exchange with rare earth. Ibid., p. 292.

Zeolites lose physically bound water to form an endotherm on heating to about 150° C. and they form exotherms around 800° C. which represent structural collapse of the zeolite. The hydroxyl groups are believed to be in different parts of the structure, some in supercages and some inaccessible to most absorbing molecules.

Zeolites can be modified to remove alumina by treatment with chelates such as acetylacetone and ethylenediamine tetraacetic acid. Aluminum atoms can be replaced with silicon tetrachloride or treatment with ammonium fluorosilicate. Ibid., p. 298. The authors of this article did not appear to contemplate the possibility of impregnation of certain small pore zeolites with alkali metal halides.

An article titled "Catalysis on Faujasite Zeolites", R. Rudham et al., Specialist Periodical Report, Chemical Society, 1977, offers an additional review of catalytic and structural properties of X and Y zeolites. They are members of the isostructural group of faujasite zeolites, which also include the rare mineral faujasite and a number of synthetic zeolites in addition to X and Y. The differences can be structurally represented by the following:

| Faujasite | $(Na_2,K_2,Mg,Ca)_{29.5}[(AlO_2)_{59}(SiO_2)_{133}]235H_2O$ |
| Zeolite X | $Na_{86}[(AlO_2)_{86}(SiO_2)_{106}]264H_2O$ |
| Zeolite Y | $Na_{56}[(AlO_2)_{56}(SiO_2)_{136}]250H_2O$ |

The term aluminum-deficient zeolite can be applied to a faujasite zeolite from which, for example, both framework aluminum and cations have been extracted by treatment with ethylenediaminetetra-acetic (EDTA).

A number of commercial applications of synthetic zeolites are discussed in "Synthetic Zeolites in Commercial Applications", R. G. Muller et al, SRI PEP Review v. 81-3-3(1982). Due to the unique structure of zeolites and to the knowledge available today regarding properties and manufacturing processes, many uses have been discovered for zeolites in adsorbent and catalytic applications. Some of the reactions for which synthetico zeolites have been shown to be active catalysts include xylene isomerization, naphtha isomerization, light olefin oligomerization, toluene dealkylation, benzene hydrogenation, olefin and fat hydrogenation, methanation, dehydrogenation of ethylbenzene, dehydrohalogenation, desulfurization and propylene carbonylation.

A good means of familiarization with the relationship between molecular shapes, structures of zeolites and selectivity for certain catalysis is available in an article titled "Industrial Application of Shape Selective Catalysis", N.Y. Chen et al., Catal. Rev.-Sci. Eng., 28 185 (1986).

The zeolites of interest to shape-selective catalysis may be divided into three major groups according to their pore/channel systems. The first group includes 8-membered oxygen ring systems such as, for example, zeolite alpha, ZK-4, ZK-21, ZK-22 and several other less common natural zeolites.

The second group includes 10-membered oxygen ring systems such as, for example, ZSM-5, ZSM-11, ZSM-22, ZSM-23, ZSM-48 and laumontite, which has a puckered 10-membered oxygen ring. The rest are considered medium pore zeolites and are usually synthetic in origin; they are sometimes known as pentasils. They have a predominance of silicon.

The third group of zeolites is those having dual pore systems which are interconnecting channels of either 12- and 8-membered oxygen ring openings or 10- and 8-membered oxygen ring openings.

An article by D. S. Shihabi et al., J. Catal., 93, 471 (1985) showed that binding of high-silica ZSM-5 with alumina enhances the catalytic activity of the catalyst for numerous reactions. In an article by C. D. Chang et al., J. Am. Chem. Soc., 106, 8143 (1984), there is reported aluminum insertion into high-silica zeolite frameworks by reaction with aluminum halides.

There are a number of different methods of achieving molecular shape selectivity. Shape selectivity can be accomplished either through reactant selectivity or product selectivity. It is believed Columbic field effects also play a part. Another phenomenon which has been observed to contribute is configurational diffusion which occurs in situations where structural dimensions of the catalyst approach those of molecules; even subtle changes in dimensions of molecules can result in large changes in diffusivity. Chen et al., Catal. Rev.-Sci. Eng., supra, p. 198.

Another type of selectivity which has been observed is spatiospecificity or restricted transition state, where both the reactant molecule and the product molecule are small enough to diffuse through channels, but the reaction intermediates are larger than either the reactants or the products and are spatially constrained. This is one of the most important properties of ZSM-5. Some zeolites, such as ZSM-5, ferrierite, cliniptilolite, offretite and mordenite have intersecting channels of differing channel size. Ibid., p.198. It is noted that these zeolites are preferred in the instant invention.

Reactants which are of interest in shape selective catalysis include hydrocarbons, paraffins, olefins, naphthenes and aromatics.

In U.S. Pat. No. 4,214,307 to C. D.Chang el al.(Jul. 22, 1980), it is shown that hydration of $C_2$ to $C_4$ olefins to alcohols can be carried out over ZSM-5 at below about 240° C. and 10 to 20 atmospheres of pressure without forming ethers or other hydrocarbons, however, above 240° C. propene and butenes undergo other olefinic reactions, forming higher molecular weight hydrocarbon products.

U.S. Pat. No. 4,760,200 provides a good background for the production of alkylene glycols. The process claimed therein is for the selective production of monoalkylene glycol which comprises reacting a vicinal alkylene oxide in liquid phase in the presence of a water-soluble metalate anion catalyst, wherein the aqueous medium also contains a water miscible ethylene glycol ether co-solvent.

In current typical alkoxylation processes, aqueous potassium hydroxide solution is commonly used as a catalyst and is reacted with alcohols to form initiators. The excess potassium hydroxide and potassium alkoxide are neutralized with a suitable organic acid such as oxalic or a mineral acid such as sulfuric acid and/or Magnesol ® magnesium silicate. The resulting salts or filter cake must then be filtered from the reaction mixture. This magnesium silicate causes both product loss and presents a waste disposal problem. Therefore, it would be very desirable to develop a solid base catalyst which could be as effective as aqueous KOH for alkoxylation.

From a review of the art available there are no descriptions of alkali metal, alkaline earth metals and alkali metal halides on certain small pore and/or dual pore zeolites, aluminas, silica/aluminas and zeolite aluminas.

Triethylene glycol is a valuable gas treating compound. It is also a useful chemical intermediate. For example, it has been used in the manufacture of triethyleneglycoldiamine. It has excellent solvent properties and is useful in reactions which require high temperatures. The triethylene glycol is typically obtained as a by-product of the reaction between ethylene oxide and water to prepare ethylene glycol. It would be preferred to prepare triethylene glycol directly such as by the reaction of diethylene glycol with one mole ethylene oxide. However, with conventional alkoxylation catalysts, the reaction is not selective and a wide distribution of products including "heavies" are formed. This cuts down on the triethylene glycol yield and results in the formation of non-useful heavy materials. Using the process of the instant invention it is possible to produce a narrow range of glycols with minimal production of bottoms.

SUMMARY OF THE INVENTION

In accordance with the foregoing, the present invention relates to a method for the production of narrow range glycols by alkoxylation of alcohols, glycols and polyalkylene glycols using a heterogeneous catalyst comprising a compound from the group consisting of alkali metals, alkaline earth metals or alkali metal halides impregnated or exchanged into an inorganic solid oxide selected from the group consisting of small pore and/or dual pore zeolites and oxides of Group III and/or IV of the Periodic Table, or mixtures thereof, at a temperature of from about 80° C. to 200° C. and a pressure of atmospheric to about 100 psig.

The catalyst is more selective toward the formation of triethylene glycol than a potassium hydroxide or barium oxide catalyst and the amount of "heavies" which are byproducts of the reaction are reduced. The heterogeneous catalyst does not require neutralization and could simply be filtered from the reaction mixture. In addition, the catalyst could be adapted to a continuous reactor.

DETAILED DESCRIPTION OF THE INVENTION

This invention describes a method of alkoxylating alcohols, glycols and polyalkylene glycols with alkylene oxides over an impregnated or exchanged inorganic solid oxide catalyst in the preparation a narrow range alcohol, glycol and polyalkylene glycol homologues.

The class of catalysts of this invention appear to be particularly useful in alkoxylations leading to narrow molecular weight range alcohols, glycols and polyalkylene glycols having 1 to 20 carbon atoms per molecule. Preferred reactants are polyalkylene glycol compounds having the general formula:

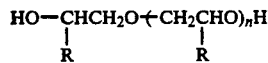

where each R is, independently, a hydrogen or a lower molecular weight alkyl radical, such as for example, methyl, ethyl or the like, and n is an integer from zero to five. Suitable polyalkylene glycols include ethylene glycol, diethylene glycol, triethylene glycol, propylene glycol, dipropylene glycols and low molecular weight JEFFOX® polyethylene glycols and JEFFOX® polypropylene glycols. The examples demonstrate the effectiveness of diethylene glycol (DEG).

Suitable alkylene oxides or epoxides which are reacted with the said alcohols, glycols and polyalkylene glycols, in the presence of said impregnated or exchanged inorganic solid oxide catalysts, are generally alkylene oxides containing 2 to 4 carbon atoms per molecule and one epoxide group per molecule. Suitable epoxides include 1,2-butylene oxide, 1,2-propylene oxide and ethylene oxide. The examples illustrate the usefulness of ethylene oxide.

Where the polyalkylene glycol reactant is a low molecular weight glycol, such as diethylene glycol (DEG) and the alkylene oxide coreactant, such as ethylene oxide (EO), is added in about stoichiometric amounts (e.g. 1 mole of EO per mole of DEG) then the principle product will be the next highest glycol homologue, in this case triethylene glycol (TEG). This particular synthesis is illustrated in Eq. (1).

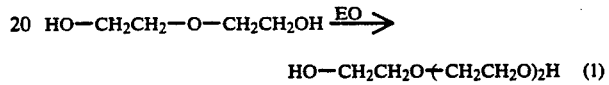

The particular advantages of the alkali metal, alkaline earth metal or alkali metal halide impregnated or exchanged inorganic solid oxide catalysts of this invention include $^a$)improved selectivity to the desired product glycol homologue (in the case of Reaction (1), TEG), and $^b$)a reduction in the amount of "heavy" by-products formed.

The catalyst employed for alkoxylation of alcohols comprises a compound selected from the group consisting of alkali metals, alkaline earth metals or alkali metal halides impregnated or exchanged into an inorganic solid oxide selected from the group consisting of zeolites having specified physical parameters, aluminas, silica/aluminas and zeolite/aluminas.

The alkali metals can be selected from Group IA of the Periodic Table, consisting of lithium, sodium, potassium, rubidium and cesium. The examples demonstrate the effectiveness of potassium and cesium.

The alkaline earth metals can be selected from Group IIA, consisting of beryllium, magnesium, calcium, strontium, barium and radium or oxides thereof. The examples demonstrate good results using barium oxide.

The alkali metal halide can be a compound containing, for example, a halide of lithium, sodium, potassium, rubidium or cesium. Examples 4 and 5 demonstrate the effectiveness of cesium chloride on a zeolite having the physical parameters described below.

The preferred compounds for impregnation or exchange into said inorganic solid oxide are potassium hydroxide, barium oxide and cesium chloride.

The inorganic solid oxides comprise specified large, intermediate or small pore zeolites having generally pore dimensions smaller than about 10 Å (see "Introduction to Zeolite Science and Practice", H. Van Bekkum et al., Studies in Science and Catalysis, No. 58, p. 632), or one or more oxides of compounds selected from Group IV of the Periodic Table. Zeolite materials which can be used as suitable matrices include certain small pore faujasites, medium pore pentasils, the small pore ferrierite, the two-dimensional large pore mordenite, large pore β-type materials and basic zeolites. Basic zeolites which are particularly effective in the instant invention are large pore X and Y zeolites, particularly the sodium form, e.g. NaX, NaY, zeolite L in potassium form (KL) and synthetic ferrierite. Also suitable are oxides of Groups III and/or IV, including oxides of aluminum, silica, titanium, zirconium, hafnium, germanium, tin and lead, as well as mixtures thereof. Particularly preferred ore oxides of aluminum and silica and mixtures thereof.

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have non-intersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottlenecks in the window/cage structure, molecules larger than the size of the channel do not form with the exception perhaps at the intersections.

Example 1 demonstrates the use of ZSM-5. ZSM-5 can be synthesized by including organic molecules such as tetrapropylammonium bromide in the reaction mixtures. The organic molecules are incorporated into the zeolite crystal interstices as the zeolite is formed. See R. J. Argauer et al., U.S. Pat. No. 3,702,886 (Nov. 14, 1972); L. D. Rollmann, Inorganic Compounds with Unusual Properties, Vol. 2 (R. B. King, ed.), Am. Chem. Soc., New York, 1979, p. 387; D. H. Olson, W. O. Haag, and R. M. Lago, J. Catal., 61, 390 (1980); G. T. Kerr, Catal. Rev.-Sci. Eng., 23, 281 (1981).

Properties of ZSM-5 which are of significance to shape-selective catalysis are the presence of two intersecting channels formed by rings of 10 oxygen atoms. The two intersecting channels, both formed by 10-membered oxygen rings, are slightly different in their pore size. One runs parallel to the a-axis of the unit cell; it is sinusoidal and has a nearly circular (5.4×5.6 Å) opening. The other runs parallel to the b-axis and has a straight, but elliptical opening (5.1×5.5 Å). See W. M. Meier and D. H. Olson, Atlas of Zeolite Structure Types, International Zeolite Assoc., Polycrystal Book Service, Pittsburgh, 1978.

Also very useful are zeolites having dual pore systems displaying interconnecting channels of either 12- and 8-membered oxygen ring openings or 10- and 8-membered oxygen ring openings. Examples are mordenite, offretite, Linde T, gmelinite, heulandite/clinoptilolite, ferrierite, ZSM-35, -38, stilbite, dachiardite, epistilbite, etc. Because the smaller channels are accessible only by the smaller molecules while the larger channels are accessible by both the large and small molecules, their catalytic properties are sometimes quite distinct from other zeolites. However, most of the natural varieties and some of the synthetic samples contain numerous stacking faults, and in many catalytic reactions they behave like small-pore zeolites. The test runs in Example 2 demonstrate the usefulness of ferrierite and mordenite.

The preferred zeolites may have dual pore systems and/or pore dimensions of about 3 to 8 Å. Specific examples of preferred supports include the pentasil ZSM-5, ferrierite, mordenite and the Y-zeolite in sodium form (NaY) in addition to alumina, silica/alumina and zeolite alumina.

The desired metals can be introduced onto the solid support by either ion exchange or impregnation. In ion exchange, metal ions can be introduced into zeolites by direct exchange of a cation into the structure from aqueous solutions of their salts such as nitrates, chlorides, acetates and the like.

Impregnation was used in the instant invention, wherein the metal compounds were dissolved in a suitable solvent such as, for example, water, aqueous ammonia, dilute phosphoric acid or others. The alkali compound is associated with the catalyst rather than a replacement of cation by cation in the exchange procedure.

The quantity of alkali metal, alkaline earth metal or alkali metal halide exchanged or impregnated into the inorganic solid oxide may vary. The reaction proceeds when employing as little as about one to 50% of said compound together with about 50 to 99 wt % zeolite or Group IV oxide, basis the total weight of the catalyst. Optionally said alkali or alkaline earth-treated zeolite or Group IV oxide may be calcined at 100°–800° C.

The temperature range which can usefully be employed is variable depending upon other experimental factors, including pressure and choice of particular species of catalysts, among other things. The range of operability is from about 80° to 200° C. A narrow range of 130° to 170° C. is preferred. The examples demonstrate that the most preferred temperature is about 140° C.

Pressures of atmospheric to 100 psig can be used. In most instances very mild pressures of about 50 psig are sufficient.

The novel catalyst can typically be introduced into an autoclave initially and the reactants can be continuously or intermittently introduced into such a zone during the course of the reaction.

The products have been identified by gas and liquid chromatography.

Various embodiments of the process of this invention are demonstrated in the following examples which are only intended to be illustrative and are not intended to limit the invention in any way.

EXAMPLE 1

This example will describe the use of ZSM-5 pentasil zeolite (from Conteka) which had been impregnated with 20 wt % KOH and calcined at 530° C. for five hours, as a catalyst in the reaction of diethylene glycol (DEG) with one mole EO to form triethylene glycol (TEG). For comparison, similar data are included for the potassium hydroxide-catalyzed reaction of DEG with 1 mole EO in the absence of any zeolite component (Example A).

Reaction changes, details of preparation and properties of products from the above reactions are as follows:

Into a 1-gallon stirred autoclave were charged 500 g DEG and 10 g potassium hydroxide-treated ZSM-5 pentasil type zeolite. The reactor was then purged with prepurified nitrogen. The DEG was then heated to 142° C. and EO addition commenced. At this point, a reaction exotherm developed and a total of 211 g EO was reacted at 150°–151° C. over a 2.8 hour period. The reaction mixture was then digested 1 hour to an equilibrium pressure at 150° C. and nitrogen stripped for 15 minutes. The reaction mixture was then cooled to 100° C. and filtered. The products were then analyzed for composition using gas chromatography (gc) and for sodium and potassium content. Results are shown in the following table. For comparison, a similar experiment run with potassium hydroxide catalyst is shown.

| Ex. | 1 | A |
|---|---|---|
| Sample No. | 6813-28 | 6813-17 |
| Product distribution, % | | Control with potassium hydroxide catalyst |
| EG | 0.15 | 0.48 |
| DEG | 32.15 | 27.0 |
| TEG | 42.03 | 41.06 |
| $T_4EG$ | 18.68 | 21.35 |
| $T_5EG$ | 4.98 | 6.68 |
| $T_6EG$ | 0.97 | 1.55 |
| $T_7EG$ | 0.14 | 0.28 |
| $T_8EG$ | 0.012 | 0.038 |
| DEG conversion, % | 67.8 | 73.0 |
| Selectivity, % | | |
| TEG | 62.0 | 56.25 |
| $T_4EG$ | 27.5 | 29.25 |
| $T_5$-$T_8$ heavier | 9.0 | 11.7 |
| Sodium, ppm | 0.1 | 0.5 |

| Ex. | 1 | A |
|---|---|---|
| Sample No. | 6813-28 | 6813-17 |
| Potassium, ppm | 29.0 | 332 |

EXAMPLES 2–4

These examples will show the use of other zeolites which had been impregnated with potassium hydroxide, to catalyze the reaction of DEG with 1 mole EO to produce TEG. As in Example 1, the zeolites were impregnated with 20 wt % potassium hydroxide and calcined at 530° C. for 5 hours.

Reaction charges, details of preparations, and product properties are shown in the following table:

| Ex. | 2 | 3 | 4 | A |
|---|---|---|---|---|
| Run No. | 6813-30 | 6313-36 | 6813-34 | 6813-17 |
| Catalyst | 20% KOH on Ferrierite | 20% KOH on EZ-320E Mordenite | 20% KOH on PQ CP-360-66 NaY | KOH (control) |
| Catalyst concentration | 2.0 | 1.0 | 1.0 | 0.1 |
| Reaction Details | | | | |
| Oxide addition time, hr. | 0.6 | 0.9 | 0.75 | 0.25 |
| Temp., °C. | 144–152 | 144–149 | 145–149 | 148–150 |
| Exotherm, yes/no | yes | yes | yes | yes |
| Oligomer Distribution | | | | |
| EG | 0.29 | 0.38 | 0.37 | 0.48 |
| DEG | 31.17 | 31.94 | 32.81 | 27.0 |
| TEG | 41.68 | 42.15 | 41.76 | 41.06 |
| $T_4EG$ | 19.02 | 18.79 | 18.05 | 21.35 |
| $T_5EG$ | 5.26 | 5.01 | 4.72 | 6.68 |
| $T_6EG$ | 1.11 | 0.986 | 0.95 | 1.55 |
| $T_7EG$ | 0.194 | 0.004 | 0.004 | 0.28 |
| $T_8EG$ | 0.028 | 0.014 | 0.11 | 0.038 |
| DEG conversion, % | 68.8 | 68.06 | 67.1 | 73.0 |
| Selectivity | | | | |
| TEG | 60.6 | 61.7 | 62.15 | 56.25 |
| $T_4EG$ | 27.6 | 27.6 | 26.9 | 29.25 |
| $T_5$-$T_8EG$ | 9.6 | 8.8 | 8.6 | 11.7 |

EXAMPLES 5–9

These examples will show the use of various Y-zeolites aluminas, and silica-aluminas which had been impregnated with barium oxide, to catalyze the reaction of DEG with 1 mole EO to form TEG. For comparison, similar data are included for barium oxide-catalyzed reaction of DEG with 1 mole EO in the absence of any zeolite, alumina, or silica-alumina, component (Example B). Reaction charges, details of preparation, and properties are shown in the following table:

| Ex. | B | 5 | 6 | 7 | 8 | 9 |
|---|---|---|---|---|---|---|
| Run No. | 6813-21 | 6813-43 | 6813-72 | 6813-74 | 6813-76 | 6813-78 |
| Catalyst | Barium Oxide | TK-753 Alumina BaO | SN-7063 Alumina BaO | PQ CP360-66 NaY BaO | CP304-37 Y/SA BaO | CP704-6SA Silica/Alumina BaO |
| Catalyst concentration | 1.26 | 2.0 | 2.0 | 2.0 | 2.0 | 2.0 |
| Reaction Details | | | | | | |
| Oxide addition time, hr. | 0.6 | 4.0 | 3.75 | 0.75 | 4.0 | 5.3 |
| Temp., °C. | 150–156 | 145–148 | 148–150 | 148–150 | 149–150 | 149–150 |
| Exotherm, yes/no | yes | no | yes | yes | no | no |
| Oligomer Distribution | | | | | | |
| EG | 0.66 | 0.17 | 0.27 | 0.17 | 0.059 | 0.12 |
| DEG | 29.16 | 37.74 | 32.84 | 26.36 | 41.96 | 26.06 |
| TEG | 39.62 | 39.19 | 41.14 | 42.31 | 39.82 | 40.99 |
| $T_4EG$ | 21.15 | 16.73 | 18.29 | 22.23 | 14.03 | 22.11 |
| $T_5EG$ | 6.20 | 4.41 | 4.91 | 6.89 | 3.07 | 6.94 |

-continued

| Ex. | B | 5 | 6 | 7 | 8 | 9 |
|---|---|---|---|---|---|---|
| Run No. | 6813-21 | 6813-43 | 6813-72 | 6813-74 | 6813-76 | 6813-78 |
| $T_6EG$ | 1.26 | 0.91 | 1.02 | 1.58 | 0.53 | 1.62 |
| $T_7EG$ | 0.189 | 0.18 | 0.20 | 0.26 | 0.59 | 0.34 |
| $T_8EG$ | 0.027 | 0.05 | 0.059 | 0.019 | — | — |
| DEG conversion, % | 70.84 | 62.26 | 67.16 | 73.64 | 58.04 | 73.9 |
| Selectivity | | | | | | |
| TEG | 55.9 | 61.8 | 61.25 | 57.46 | 68.6 | 55.4 |
| $T_4EG$ | 29.85 | 26.4 | 27.24 | 30.19 | 24.2 | 29.8 |
| $T_5-T_8EG$ | 10.8 | 8.75 | 9.21 | 11.9 | 6.4 | 12.2 |

EXAMPLE 10

This example will show the use of a β-zeolite (from Conteka) which had been impregnated with 20 wt % cesium chloride and calcined at 530° C. for 5 hours, as a catalyst in the reaction of DEG with 1 mole EO to make TEG. For comparison, similar data are included for the potassium hydroxide-catalyzed reaction of DEG with 1 mole EO (Example A).

Reaction charges, details of preparation and properties of products from the above reactions are as follows: Into a 1-gallon stirred autoclave were charged 500 g DEG and 10 g cesium chloride impregnated CONTEKA β-zeolite. The reactor was then purged with prepurified nitrogen. The reactor was then heated to 143° C. and 211g EO added at 143° C. at 48 psig over a 0.67 hour period. At this point, a reaction exotherm developed and the reaction mixture was digested at 153°–154° C. to an equilibrium pressure. The reaction mixture was then stripped with nitrogen for 30 minutes and filtered from the kettle. The product was then analyzed using gas chromatography (gc) and cesium and potassium content. Comparative data are shown for a potassium hydroxide-catalyzed run.

| Ex. | 10 | A |
|---|---|---|
| Sample No. | 6813-38 | 6813-17 |
| Oligomer distribution, % | | control with potassium hydroxide catalyst |
| EG | 0.21 | 0.48 |
| DEG | 31.33 | 17.0 |

-continued

| Ex. | 10 | A |
|---|---|---|
| Sample No. | 6813-38 | 6813-17 |
| TEG | 41.39 | 41.06 |
| $T_4EG$ | 19.0 | 21.35 |
| $T_5EG$ | 5.14 | 6.68 |
| $T_6EG$ | 1.03 | 1.55 |
| $T_7EG$ | 0.154 | 0.28 |
| $T_8EG$ | — | 0.038 |
| DEG conversion, % | 68.67 | 73.0 |
| Selectivity | | |
| TEG | 60.3 | 56.25 |
| $T_4-T_8$ EG | 27.7 | 29.25 |
| $T_5-T_8$ EG | 9.2 | 11.7 |
| Potassium, ppm | 2.7 | 0.5 |
| Cesium, ppm | 1.0 | 332 |

EXAMPLES 11–13

This example will illustrate the use of various cesium chloride-impregnated zeolites to promote the reaction of DEG with 1 mole EO to produce TEG. As in Example 1, the zeolites were impregnated with cesium chloride and calcined 5 hours at 1000° F.

Using the procedure of Example 1, the runs may be summarized as follows:

| Ex | 11 | 12 | 13 | A |
|---|---|---|---|---|
| Run No. | 6813-40 | 6813-63 | 6813-70 | 6813-17 |
| Catalyst | 20% CsCl on UOP KL zeolite L | 20% CsCl on UOP SAPO-34 zeolite | 20% CsCl on PQ 360-66 NaY | KOH (control) |
| Catalyst concentration, % | 1.0 | 2.0 | 2.0 | 0.1 |
| Reaction Details | | | | |
| Oxide addition time, hr | 2.0 | 2.0 | 0.6 | 0.25 |
| Temperature, °C. | 142–152 | 148–152 | 150–153 | 148–150 |
| Exotherm, yes/no | yes | no | yes | yes |
| Oligomer-Distribution | | | | |
| EG | 0.11 | — | 0.12 | 0.48 |
| DEG | 36.59 | 36.99 | 32.28 | 27.0 |
| TEG | 41.78 | 36.8 | 42.43 | 41.06 |
| $T_4EG$ | 16.53 | 17.26 | 18.3 | 21.35 |
| $T_5EG$ | 3.98 | 5.16 | 4.67 | 6.68 |
| $T_6EG$ | 0.71 | 1.18 | 0.87 | 1.55 |
| $T_7EG$ | 0.096 | 0.22 | 0.12 | 0.28 |
| $T_8EG$ | 0.006 | 0.043 | 0.007 | 0.038 |
| DEG conversion, % | | | | |
| Selectivity % | | | | |
| TEG | 65.9 | 58.4 | 67.3 | 56.25 |
| $T_4EG$ | 26.1 | 27.5 | 29.0 | 29.25 |
| $T_5-T_8EG$ | 7.55 | 10.5 | 9.0 | 11.7 |

What is claimed:

1. A process for producing narrow molecular weight range glycols which comprises:
   reacting an alkylene glycol with ethylene oxide in the presence of a heterogeneous catalyst selected from the group consisting of an alkali metal from Group IA of the Periodic Table, a halide of an alkali metal, an alkaline earth metal from Group IIA of the Periodic Table or an oxide of an alkaline earth metal impregnated or exchanged into an inorganic solid oxide consisting of a zeolite selected from the group consisting of pentasils, ferrierite, mordenite and zeolite L having pores less than about 10 Å in size, or an oxide of an element of Group III of the Periodic Table, or mixture thereof at a temperature of about 80° C. to 200° C. and a pressure of atmospheric to 100 psig.

2. The process of claim 1 wherein the glycol reactant is diethylene glycol and the product glycol is triethylene glycol.

3. The process of claim 1 wherein the alkali metal is selected from the group consisting of lithium, sodium, potassium, rubidium and cesium.

4. The process of claim 1 wherein the alkali metal is selected from the group consisting of potassium and cesium.

5. The process of claim 1 wherein the alkaline earth metal is selected from the group consisting of beryllium, magnesium, calcium, strontium and barium.

6. The process of claim 5 wherein the alkaline earth metal is barium.

7. The process of claim 1 wherein the alkali metal halide is selected from the group consisting of lithium, sodium, potassium, rubidium or cesium.

8. The process of claim 7 wherein the alkali metal halide is cesium chloride.

9. The process of claim 1 wherein the basic zeolite is L.

10. The process of claim 1 wherein the solid oxide is a zeolite having pore dimensions of about 3 to 8 Å.

11. The process of claim 1 wherein the solid oxide is a zeolite selected from the group consisting of ZSM-5, ferrierite, mordenite and L.

12. The process of claim 2, wherein the solid oxide is alumina.

13. The process of claim 1 wherein the operating temperature is from about 130° C. to 170° C.

* * * * *